United States Patent
Kim et al.

(10) Patent No.: US 11,928,251 B2
(45) Date of Patent: Mar. 12, 2024

(54) MOTION SICKNESS REDUCTION METHOD AND APPARATUS FOR VR MOTION PLATFORM

(71) Applicant: 3D INTERACTIVE CO., LTD., Daejeon (KR)

(72) Inventors: Dong-Hyuk Kim, Daejeon (KR); Bok-Dong Choi, Daejeon (KR); Jong-Deok Lee, Daejeon (KR)

(73) Assignee: 3D INTERACTIVE CO., LTD., Daejeon (KR)

( * ) Notice: Subject to any disclaimer, the term of this patent is extended or adjusted under 35 U.S.C. 154(b) by 0 days.

(21) Appl. No.: 17/296,213

(22) PCT Filed: Aug. 28, 2019

(86) PCT No.: PCT/KR2019/011027
§ 371 (c)(1),
(2) Date: May 21, 2021

(87) PCT Pub. No.: WO2020/105849
PCT Pub. Date: May 28, 2020

(65) Prior Publication Data
US 2022/0011854 A1  Jan. 13, 2022

(30) Foreign Application Priority Data
Nov. 23, 2018 (KR) .................. 10-2018-0146233

(51) Int. Cl.
*G06F 3/01* (2006.01)
*G05B 13/02* (2006.01)

(52) U.S. Cl.
CPC ............ *G06F 3/011* (2013.01); *G05B 13/024* (2013.01); *G06F 3/016* (2013.01); *G06F 3/017* (2013.01)

(58) Field of Classification Search
CPC .......... G06F 3/011; G06F 3/016; G06F 3/017; G06F 3/0426; G06F 3/0428;
(Continued)

(56) References Cited

U.S. PATENT DOCUMENTS 9,999,835 B2 * 6/2018 Watson .................. G16H 50/20
10,725,534 B2 * 7/2020 Son ........................ G06T 19/006
(Continued)

FOREIGN PATENT DOCUMENTS

JP     2004-024301 A     1/2004
KR    10-1564964 B1    11/2015
(Continued)

*Primary Examiner* — Vijay Shankar
(74) *Attorney, Agent, or Firm* — Maschoff Brennan

(57) ABSTRACT

Disclosed is a method comprising the steps of: receiving an input of content motion data included in VR content; transmitting, to a motion device, motion control data corresponding to the input content motion data to control movement of the motion device; receiving, from a predetermined sensing apparatus, motion detection data corresponding to a movement state of the motion device; selecting a motion sickness-causing section by using a difference between the motion control data and the motion detection data; generating final motion control data according to a preset algorithm such that the level of motion sickness in the selected motion sickness-causing section is minimized during a preset content reproduction section, and storing the generated final motion control data; and when 3D VR content is reproduced, transmitting, to the motion device, the final motion control data stored in the previous step so as to control the movement of the motion device.

15 Claims, 9 Drawing Sheets

(58) Field of Classification Search
CPC ........... G05B 13/024; A61B 5/02; A61B 5/11; A61B 5/721; G06Q 50/10; G06T 19/00; G06T 19/003; H04N 13/332; H04N 13/366; H04N 13/371; H04N 13/373; H04N 13/376; H04N 13/378; H04N 13/38

See application file for complete search history.

(56) References Cited

U.S. PATENT DOCUMENTS

| | | | | |
|---|---|---|---|---|
| 2014/0176296 A1* | 6/2014 | Morgan | ................ | G06F 3/011 340/4.13 |
| 2016/0027141 A1* | 1/2016 | Patel | ........................ | G06T 1/20 345/522 |
| 2016/0228771 A1 | 8/2016 | Watson | | |

FOREIGN PATENT DOCUMENTS

| | | |
|---|---|---|
| KR | 10-2016-0113491 A | 9/2016 |
| KR | 10-2017-0106162 A | 9/2017 |

* cited by examiner

MOTION SICKNESS REDUCTION METHOD AND APPARATUS FOR VR MOTION PLATFORM

FIELD OF INVENTION

The present invention relates to a motion sickness reduction method and apparatus for a virtual reality (VR) motion platform, and more particularly to a method and apparatus for minimizing motion sickness of a user when a VR motion platform for generating motion is used when three-dimensional (3D) VR content is reproduced.

BACKGROUND OF INVENTION

Recently, services using virtual reality (VR) have been increasingly used, and for example, virtual reality content has been increasingly provided not only for training purposes, such as parachuting, but also for entertainment purposes such as games.

Virtual reality is created by artificial technology using computer systems, etc., and refers to a specific environment or situation that is similar to reality but is not real, or the technology itself.

In particular, 3D virtual reality content evokes the illusion that a user watching the content is present in a three-dimensional space created by computer graphics rather than real life, and a system for a service for providing such 3D virtual reality content broadly includes a computer, a head mounted display (HMD), and a motion platform.

Here, the computer and the HMD create a virtual image environment, and the motion platform device allows people to recognize a motion sensation similar to that of a virtual environment device.

Humans feel a sense of reality more because they receive a sense of motion similar to that of a virtual environment device. Problems arise in that, generally, there are companies for providing VR content and companies for providing motion platforms, so there is often a sense of unfamiliarity between a sense of motion and an image.

That is, a motion platform is not considered when VR content is manufactured, and thus a sense of unfamiliarity with an image occurs depending on a response rate and a motion range of the motion platform, which is a major cause of user dizziness.

Accordingly, there has been a need for technology for minimizing dizziness of a user of such VR content.

SUMMARY OF INVENTION

Technical Problem to be Solved

Therefore, the present invention has been made in view of the above problems, and it is one object of the present invention to provide an apparatus and method for minimizing motion sickness of a user when watching immersive virtual reality (VR) content.

Technical Solution

In accordance with one aspect of the present invention, provided is a motion sickness reduction apparatus for a virtual reality (VR) motion platform, including a content motion data input unit configured to receive content motion data included in VR content, a motion device controller configured to transmit motion control data corresponding to the content motion data received by the content motion data input unit to a motion device and controlling motion of the motion device, a sensing data receiver configured to receive motion detection data corresponding to a motion state of the motion device from a predetermined sensing device, a motion sickness-causing section selector configured to select a motion sickness-causing section using a difference between the motion control data and the motion detection data; and a final motion control data generator configured to generate final motion control data for minimizing a degree of motion sickness in the motion sickness-causing section selected by the motion sickness-causing section selector according to a preset algorithm and to store the final motion control data, wherein the motion device controller transmits the final motion control data to the motion device and controlling motion of the motion device when three-dimensional (3D) VR content is reproduced and processed.

In accordance with another aspect of the present invention, provided is a control method of a motion sickness reduction apparatus for a virtual reality (VR) motion platform, including receiving content motion da included in VR content, transmitting motion control data corresponding to the content motion data received in the above operation to a motion device and controlling motion of the motion device, receiving motion detection data corresponding to a motion state of the motion device from a predetermined sensing device, selecting a motion sickness-causing section using a difference between the motion control data and the motion detection data, generating final motion control data for minimizing a degree of motion sickness in the motion sickness-causing section selected in the above operation during a preset content reproduction section according to a preset algorithm and storing the final motion control data, and transmitting the final motion control data stored in the above operation to the motion device and controlling the motion of the motion device when three-dimensional (3D) VR content reproduced and processed.

BEST MODE

Hereinafter, the present invention will be described in detail.

Hereinafter, embodiments of the present invention are merely examples to aid in understanding of the present invention, and the present invention is not limited to these examples. In particular, the present invention may be configured with a combination of at least one of individual configurations, individual functions, or individual steps included in each embodiment.

In particular, for convenience, some claims include letters such as '(a)', but these letters do not prescribe the order of steps.

In addition, each signal described in embodiments of the present invention may mean one signal transmitted through a single time of connection but may mean a series of signal groups transmitted for performing a specific function to be described later. That is, in each embodiment, a plurality of signals transmitted at predetermined time intervals or transmitted after receiving a response signal from a counterpart device may be expressed as a single signal name for convenience.

Figure 1:
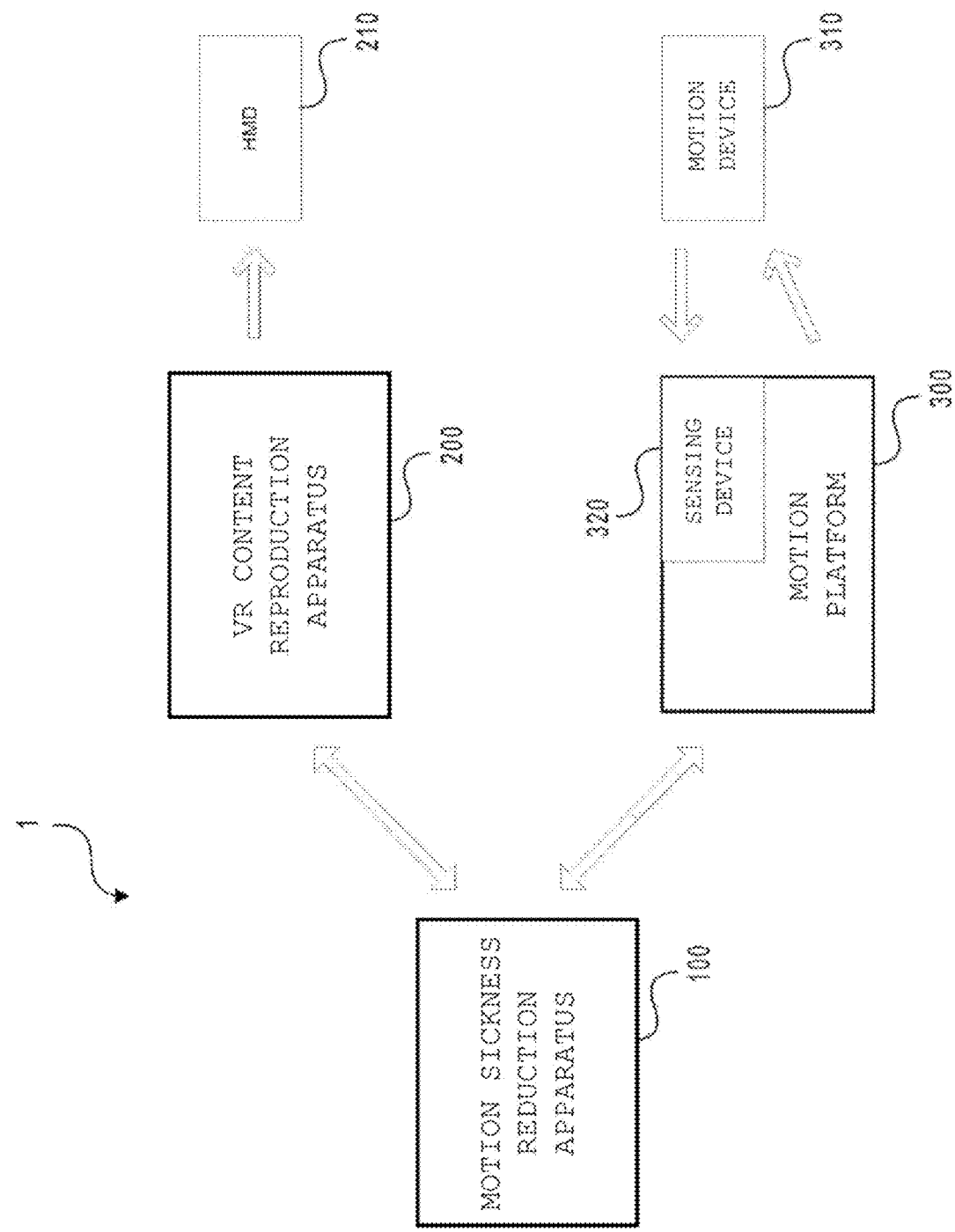
FIG. 1 is a schematic diagram showing an overall system including a motion sickness reduction apparatus according to an embodiment of the present invention.

A schematic configuration of an overall system for reproducing immersive VR content including an apparatus for reducing motion sickness for a virtual reality (VR) motion platform (hereinafter referred to as a motion sickness reduction apparatus 100) according to an embodiment of the present invention is shown in FIG. 1.

As shown in the drawing, the overall system may include the motion sickness reduction apparatus 100, a VR content reproduction apparatus 200, and a motion platform 300.

Here, the VR content reproduction apparatus 200 may reproduce and display VR content, and may perform a function of transmitting the VR content to a display device (e.g., a HMD 210) worn by a user who uses immersive VR content while extracting and reproducing stored VR content.

Accordingly, users who wear the HMD 210 may watch the VR content.

The VR content may include data for operating a motion device 310, i.e., content motion data as described below, and the VR content reproduction apparatus 200 may perform a function of extracting the content motion data included in the VR content and transmitting the same to the motion sickness reduction apparatus 100. Here, the content motion data may be data corresponding to an image viewed on a VR content screen, and for example, when VR content is photographed from a person's point of view using a parachute, the VR content may be changed depending on a direction in which a corresponding photographer views.

The VR content includes the content motion data, and a function of extracting and providing the content motion data corresponds to known technology, and a detailed description thereof is omitted.

The motion platform 300 may perform a function of operating the motion device 310 (e.g., a motor) already included therein according to a predetermined control signal.

For example, upon receiving predetermined motion control data corresponding to the aforementioned content motion data, the motion platform 300 may perform a function of controlling the motion device 310 already included therein and connected thereto according to the motion control data.

Here, as described above, the motion device 310 may move the body, arm, leg, etc. of a viewer who wears the HMD 210 and watches the VR content according to a scene of the VR content, and for example, may be configured in the form of a chair for the viewer of the VR content to sit on or may be installed on a part of the body of the viewer of the VR content.

The motion device 310 is known technology, and thus a detailed description thereof will be omitted.

The motion platform 300 may include a predetermined sensing device 320, and the sensing device 320 may detect a motion state of the motion device 310 and may generate a sensing signal based on the motion state, and for example, the sensing device 320 may perform a function of detecting a rotation state of a motor corresponding to the motion device 310 and generating a sensing signal corresponding to the rotation state.

Although FIG. 1 illustrates an example in which the sensing device 320 is included in the motion platform 300, the sensing device 320 may be configured as an independent device from the motion platform 300, and needless to say, may also be included in the motion sickness reduction apparatus 100.

The motion sickness reduction apparatus 100 may communicate with the VR content reproduction apparatus 200 and the motion platform 300, may receive the content motion data from the VR content reproduction apparatus 200, and may perform a function of generating the motion control data corresponding to the received content motion data and transmitting the motion control data to the motion platform 300.

For example, the motion sickness reduction apparatus 100 may generate the motion control data for controlling the motion device 310 to move in the same direction as a direction in which the motion device 310 moves on the VR content photographed from a first person view based on the content motion data included in the VR content and may provide the generated motion control data to the motion platform 300.

Accordingly, a viewer who wears the HMD 210 and views the VR content may feel their body moving when watching VR content, and thus the immersive effect may be maximized.

For example, when the VR content is photographed from a first person view of a roller coaster, the viewer of the VR content may move his or her body according to a motion of the motion device 310 corresponding to a scene on the VR content screen, and accordingly, the viewer may have the same experience as riding on a real roller coaster.

In this case, the motion sickness reduction apparatus 100 may use the content motion data without change as the motion control data and may transmit the content motion data to the motion platform 300, or may also generate the motion control data corresponding to the content motion data using a separate driving driver for each motion device 310 and may transmit the generated motion control data to the motion platform 300.

Such a function of the motion sickness reduction apparatus 100, that is, transmission of the motion control data corresponding to the content motion data to the motion platform 300 may correspond to known technology, and hereinafter, a function of the motion sickness reduction apparatus 100 differentiated from the prior art will be described with reference to FIG. 2.

Figure 2:
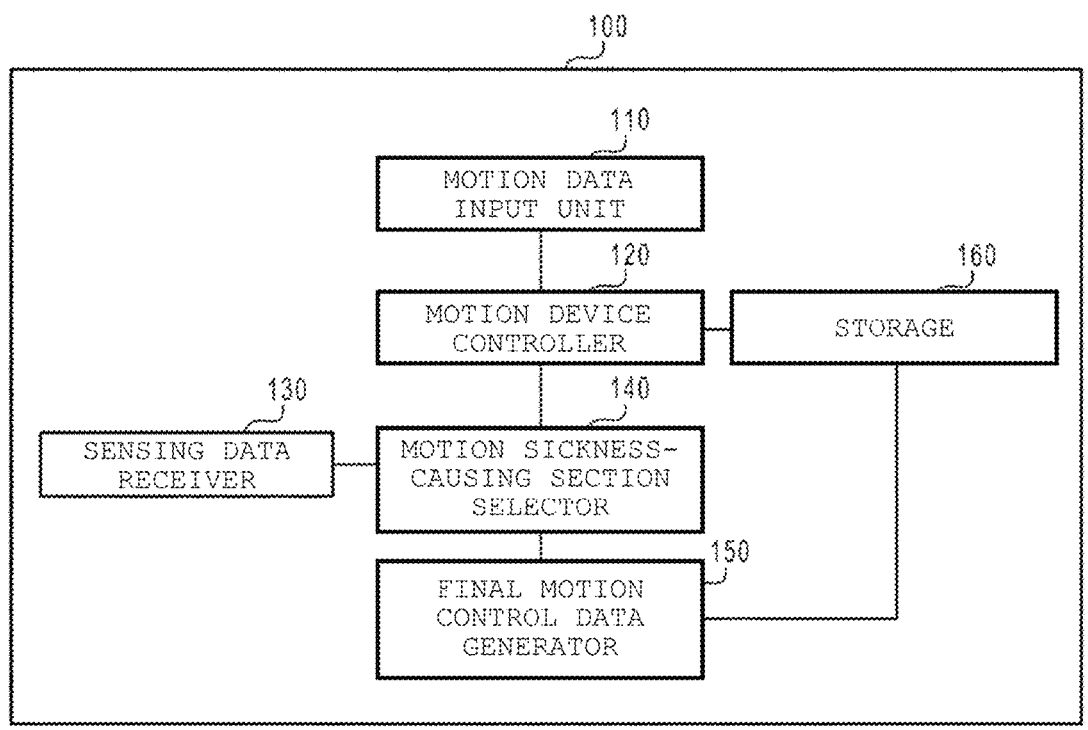
FIG. 2 is a functional block diagram of the motion sickness reduction apparatus of FIG. 1.

As shown in FIG. 2, the motion sickness reduction apparatus 100 according to an embodiment of the present invention may include a motion data input unit 110, a motion device controller 120, a sensing data receiver 130, a motion sickness-causing section selector 140, a final motion control data generator 150, and a storage 160.

Here, the storage 160 may include data, information, a program, etc. required for an operation of the motion sickness reduction apparatus 100, and in particular, may also perform a function of additionally storing data, information, etc. that are generated during an operation of the motion sickness reduction apparatus 100 or are received from the outside.

The content motion data input unit 110 may perform a function of receiving the content motion data included in the VR content, for example, three-dimensional (3D) VR content.

As described above, the VR content reproduction apparatus 200 may perform a function of extracting the content motion data from 3D content included therein and transmitting the extracted content motion data, and the content motion data input unit 110 may perform a function of receiving the content motion data from the VR content reproduction apparatus 200.

According to the present embodiment, the motion sickness reduction apparatus 100 and the VR content reproduction apparatus 200 are separately configured, and in this case, a function of the VR content reproduction apparatus 200 may be included in the motion sickness reduction apparatus 100, and in this case, when a predetermined content reproducer (not shown) reproduces and processes 3D content, the content motion data input unit 110 may also receive the content motion data from the content reproducer.

The motion device controller 120 may transmit the motion control data corresponding to the content motion data input to the content motion data input unit 110 to the motion device 310 and may perform a function of controlling a motion of the motion device 310. As such, transmission of the motion control data to the motion device 310 may correspond to known technology as described above.

The motion device controller 120 may transmit the final motion control data stored in the storage 160 to the motion device 310 and may perform a function of controlling a motion of the motion device 310 when the 3D VR content is reproduced and processed, and the final motion control data will be described below in more detail.

The sensing data receiver 130 may perform a function of receiving the motion detection data corresponding to the motion state of the motion device 310 from the predetermined sensing device 320. That is, as described above, the sensing device 320 may detect the motion state (a motion angle, a motion speed, a moving distance, etc.) of the motion device 310, may perform a function of generating and transmitting a kind of sensing data, that is, the motion detection data based on the motion state, and reception of the information may be performed by the sensing data receiver 130.

The motion sickness-causing section selector 140 may perform a function of determining a motion sickness-causing section using a difference between the motion control data and the motion detection data.

For example, the motion sickness-causing section selector 140 may select the motion sickness-causing section based on a section in which the size of the motion detection data is not changed while the size of the motion control data is changed.

For example, when a motion range of the motion device 310 is exceeded while the motion device 310 operates according to the motion control data, even if the motion control data is input, the corresponding motion device 310 may not move any longer, and in this case, as described above, the size of the motion detection data may not be changed while the size of the motion control data is changed, and the motion sickness-causing section selector 140 may select such a section as the motion sickness-causing section.

For example, when the motion device 310 is in the motion range, the motion detection data may also have a sine curve according to the content motion data of a sine curve (a sine curve of a trigonometric function), and in this regard, upon receiving content motion data outside the range of motion of the motion device 310, the corresponding motion device 310 may stop at the maximum motion range, and accordingly, the motion detection data may not follow the sine curve of the content motion data any longer.

As the experimental result according to the present applicant, when a person moves his or her body according to movement in a watched image, he or she may experience less dizziness, and accordingly, according to the present embodiment, the motion sickness-causing section selector 140 may determine the motion sickness-causing section based on a difference between the content motion data and the motion detection data, and in particular, a section in which the size of the motion detection data is not changed while the size of the motion control data is changed may be selected as the motion sickness-causing section.

Here, the 'section' may refer to a section in the time domain in the state in which VR content is reproduced.

In another example, the motion sickness-causing section selector 140 may also select the motion sickness-causing section based on the section in which a difference between change in the motion control data and change in the motion detection data is equal to or less than a preset value.

That is, like in the aforementioned example, the section in which the motion detection data is not changed at all but change in the motion detection data is equal to or less than a preset value may also be selected as the motion sickness-causing section.

The final motion control data generator 150 may perform a function of generating final motion control data for minimizing a degree of motion sickness in a preset content reproduction section according to a preset algorithm in the motion sickness-causing section selected by the motion sickness-causing section selector 140 and storing the generated final motion control data in the storage 160.

For example, as described above, when the motion sickness-causing section selector 140 selects the motion sickness-causing section based on a section in which the size of the motion detection data is not changed while the size of the motion control data is changed, the final motion control data generator 150 may adjust the motion control data to continuously change the size of the motion detection data in the motion sickness-causing section and may generate and store the adjusted motion control data as final motion control data.

In another example, when the motion sickness-causing section selector 140 selects the motion sickness-causing section based on a section in which a difference between change in the motion control data and change in the motion detection data is equal to or less than a preset value, the final motion control data generator 150 may adjust the motion control data to increase the change in the motion detection data in the motion sickness-causing section compared with a preset value and may generate and store the adjusted motion control data as final motion control data.

A detailed embodiment in which the motion control data is corrected or changed to generate the final motion control data will now be described. First, the final motion control data generator 150 may calculate the final motion control data by multiplying motion control data in a specific section including the motion sickness-causing section by a magnification value less than or equal to 1. Here, the specific value may be the same as the motion sickness-causing section or may also be a section extending left and right in a predetermined time unit based on the motion sickness-causing section.

In this case, the change amplitude of the final motion control data may become smaller than the change amplitude of the motion control data.

Here, the magnification value may be dynamically calculated in consideration of a difference between the motion control data and the motion detection data in the motion sickness-causing section and the size of the motion control data in a specific section including the motion sickness-causing section.

In another example, the final motion control data generator 150 may also generate the final motion control data by performing filter processing of a frequency domain on the motion control data of a specific section including the motion sickness-causing section.

For example, when filtering processing of the frequency domain corresponds to a low pass filter, a change frequency of the final motion control data may be lower than a change frequency of the motion control data.

In another example, the final motion control data generator 150 may also generate the final motion control data by adding or subtracting a delay value to or from the motion control data in a specific section including the motion sickness-causing section.

When the motion device 310 is a device that performs three-dimensional movement, the aforementioned motion control data and final motion control data may be used to control the motion device 310 to perform at least one of X-axis rotation, Y-axis rotation, or Z-axis rotation in 3D coordinates.

Here, rotation about the respective axes may also be represented by PITCH, ROLL, and YAW.

As such, when VR content is executed in the state in which the final motion control data is stored in the storage 160, the aforementioned motion device controller 120 may extract the stored final motion control data and may transmit the same to the motion platform 300.

Accordingly, the motion device 310 may perform an operation based on the final motion control data, and thus the likelihood of a VR viewer experiencing motion sickness is reduced.

Figure 3:
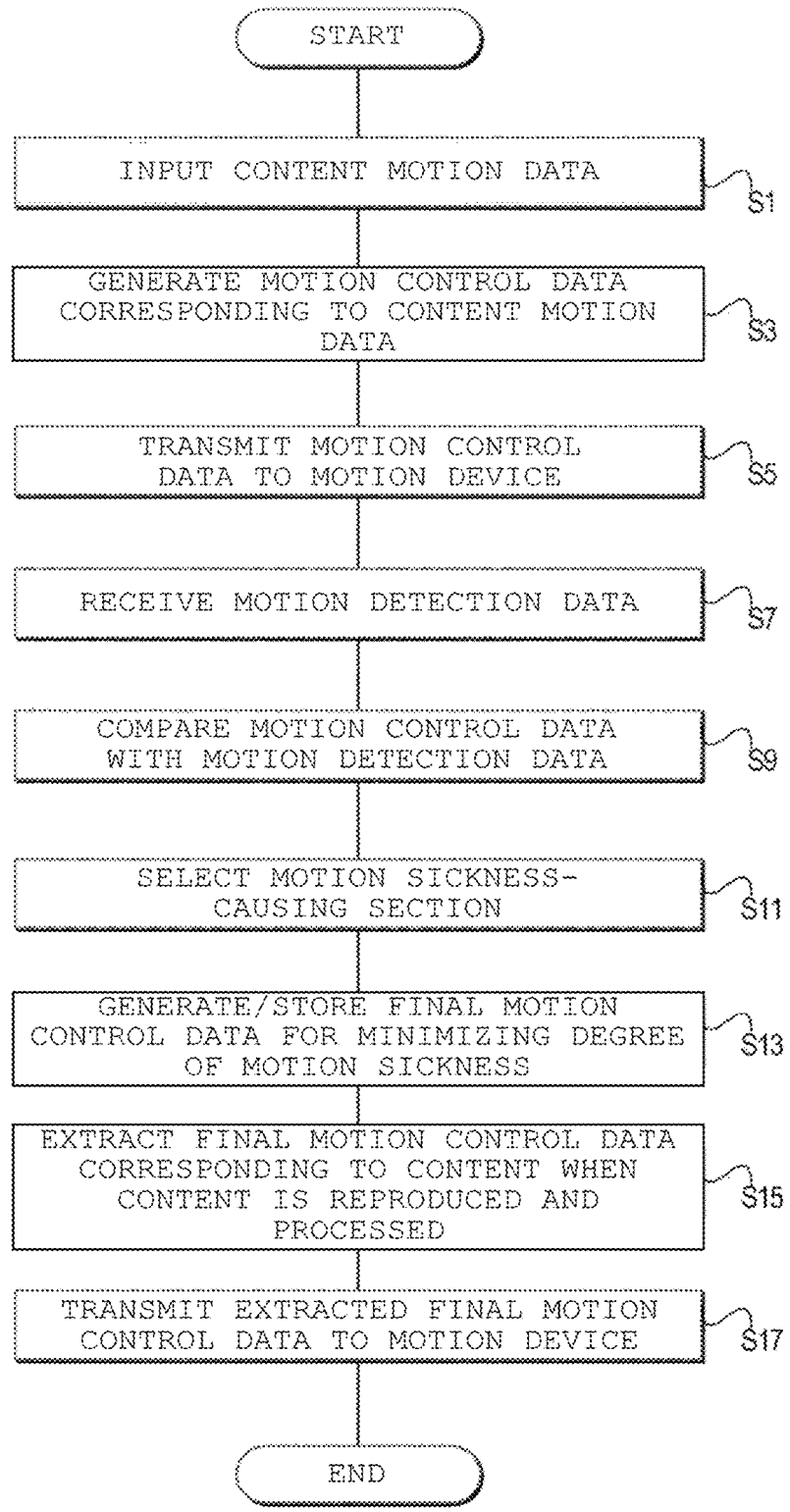
FIGS. 3 and 4 are control flowcharts of a motion sickness reduction apparatus according to an embodiment of the present invention.

Hereinafter, an overall control procedure of the motion sickness reduction apparatus 100 according to an embodiment of the present invention will be described with reference to FIG. 3.

First, the motion sickness reduction apparatus 100 may receive content motion data from the VR content reproduction apparatus 200 and may generate motion control data corresponding to the content motion data.

Then, the motion sickness reduction apparatus 100 may transmit the generated motion control data to the motion device 310, and as described above, when the motion device 310 is not controlled directly, the generated motion control data may also be transmitted to the motion platform 300.

Accordingly, the motion device 310 may be driven, and upon receiving the motion detection data from the sensing device 320 or a sensor for detecting an operation or driving state of the motion device 310, the motion sickness reduction apparatus 100 may compare the received motion detection data and the motion control data or a variation therebetween.

Through such comparison, the motion sickness reduction apparatus 100 may select the motion sickness-causing section on the time axis and may generate the final motion control data for minimizing a degree of motion sickness in the corresponding motion sickness-causing section and may store the same in the storage 160.

Then, when reproducing and processing the VR content, the motion sickness reduction apparatus 100 may extract the final motion control data corresponding to the VR content from the storage 160 and may transmit the same to the motion device 310 or the motion platform 300.

That is, in the present embodiment, operation S5 may be a type of test driving operation of the motion device 310, and operation S17 may be an actual use operation for controlling the motion device 310 when a user watches actual VR content.

Accordingly, although not shown, the motion sickness reduction apparatus 100 may first classify the test operation and the actual use operation and may also perform automatic processing accordingly.

For example, upon receiving content motion data from the VR content reproduction apparatus 200, the motion sickness reduction apparatus 100 may check whether final motion control data corresponding to the corresponding VR content is stored in the storage 160, and as the check result, when the final motion control data is not stored, the aforementioned final motion control data generation procedure (a procedure of determining the motion sickness-causing section and generating the final motion control data for minimizing a degree of motion sickness in the section), and as the check result, when the final motion control data is already stored, a procedure of extracting the stored final motion control data from the storage 160 and transmitting the same to the motion device 310 or the motion platform 300 may be performed.

To this end, when the content motion data is received from the VR content reproduction apparatus 200, an identifier for specific the corresponding VR content may be received therewith, and information on whether the final motion control data corresponding to specific VR content is present may be determined and extracted when the specific VR content is reproduced by matching the content identifier with the final motion control data and storing the same.

Needless to say, the test operation and the actual use operation may be classified according to a command or selection of a manager.

The following effect may be achieved through such procedures.

For example, when the motion device 310 is controlled using the final motion control data when VR content is reproduced after the final motion control data is calculated by multiplying the motion control data in the specific section including the motion sickness-causing section by a magnification value equal to or less than 1 and storing the same, the motion device 310 may reduce a movement magnitude degree (amplitude degree) but may prevent the case in which the motion device 310 stops as exceeding the motion range compared with the case in which the motion device 310 is controlled using the motion control data corresponding to existing content motion data.

That is, a user who uses immersive VR content may feel less body movement in the same VR content viewing section, the number of stops of movement will be considerably reduced, and accordingly, the likelihood of motion sickness may be considerably reduced like in the result obtained through the test.

Figure 5:
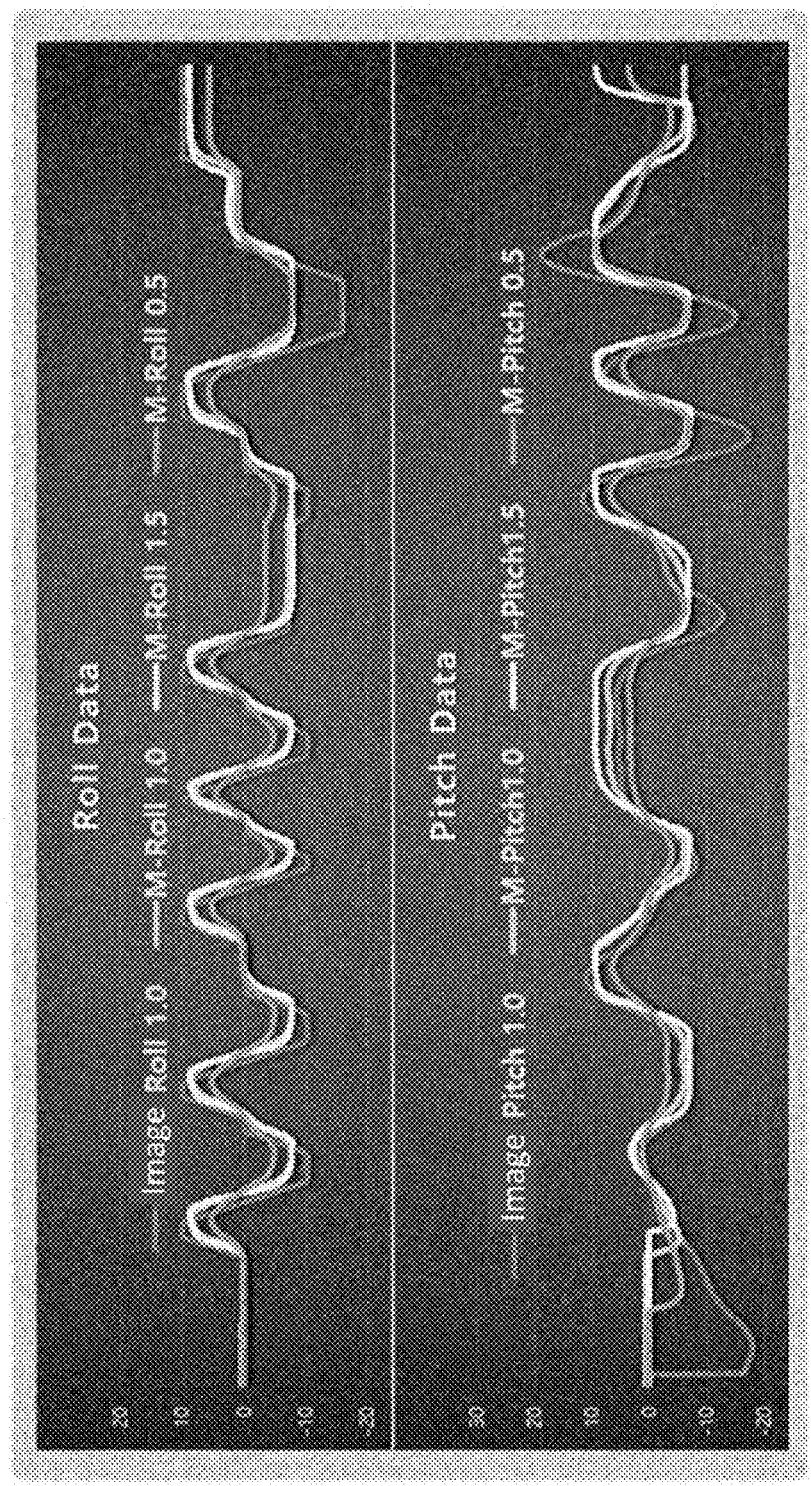
FIG. 5 is a diagram showing examples of motion detection data when a motion device is controlled using final different motion control data values.

For reference, FIG. 5 illustrates the result value of the final motion control data calculated by applying the motion control data and each magnification value, that is, motion detection data.

FIGS. 6 to 9 show plots for each situation in FIG. 5.

Figure 6:
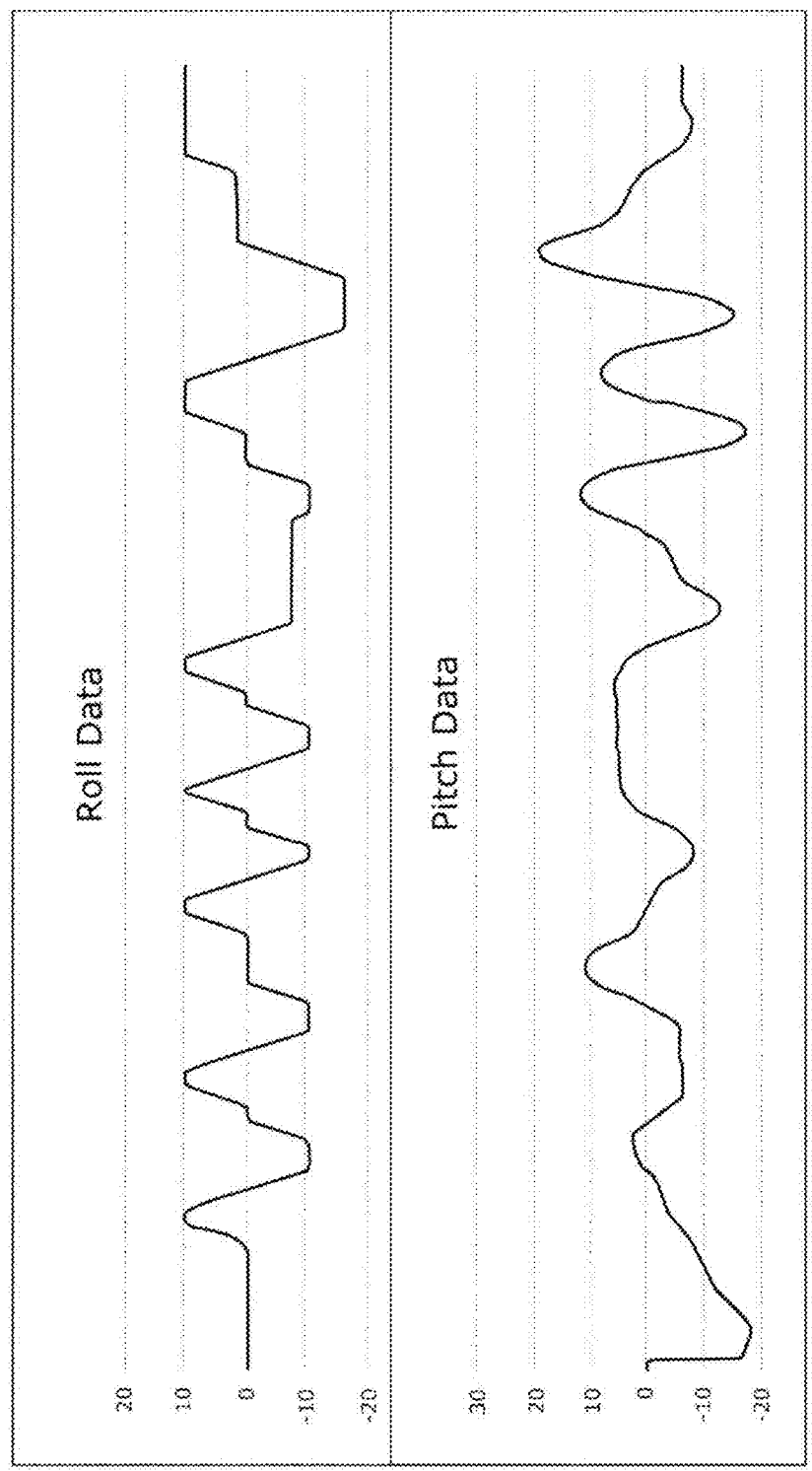
FIGS. 6 to 9 are diagrams showing separate plots for each situation in FIG. 5.
Figure 7:
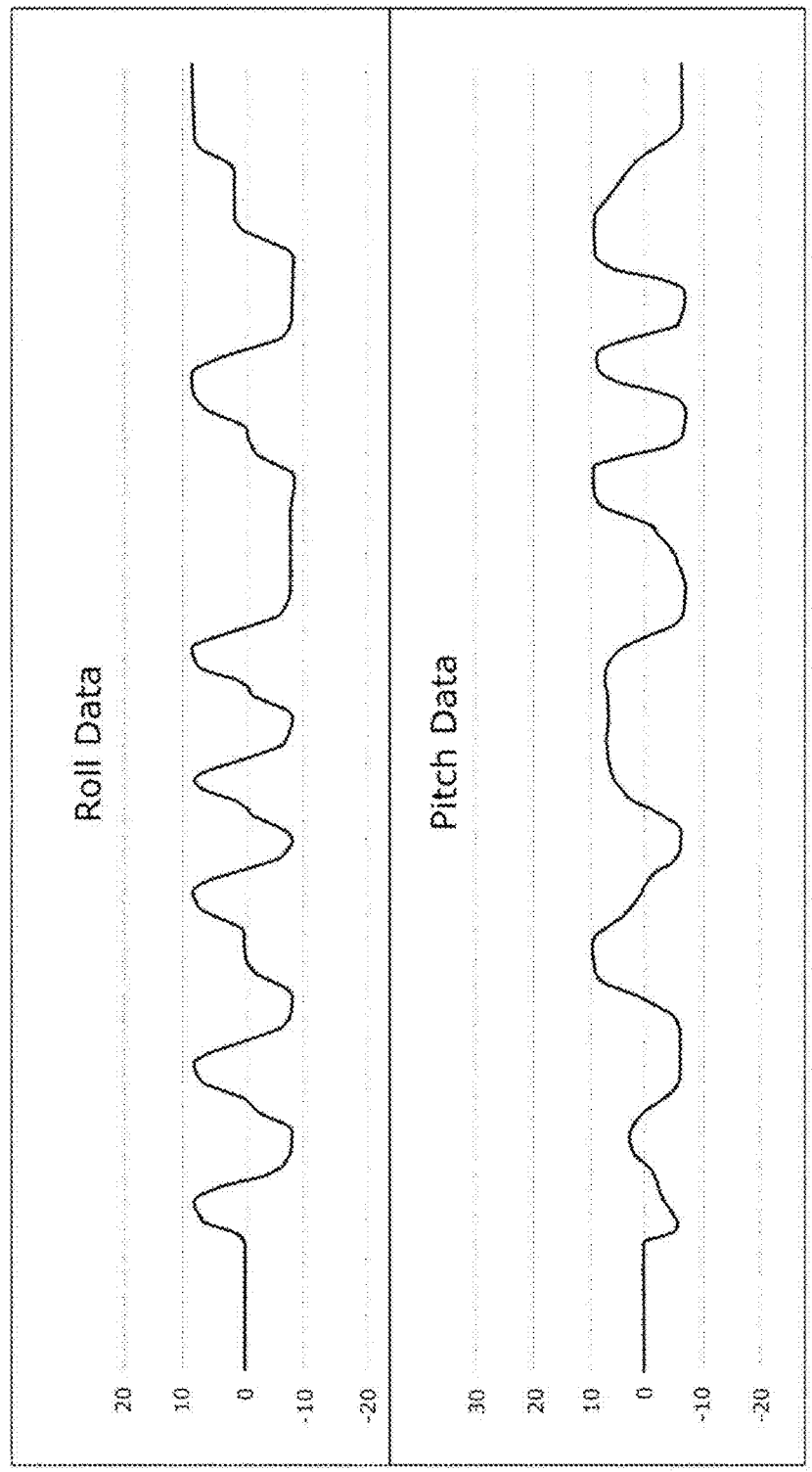
Figure 8:
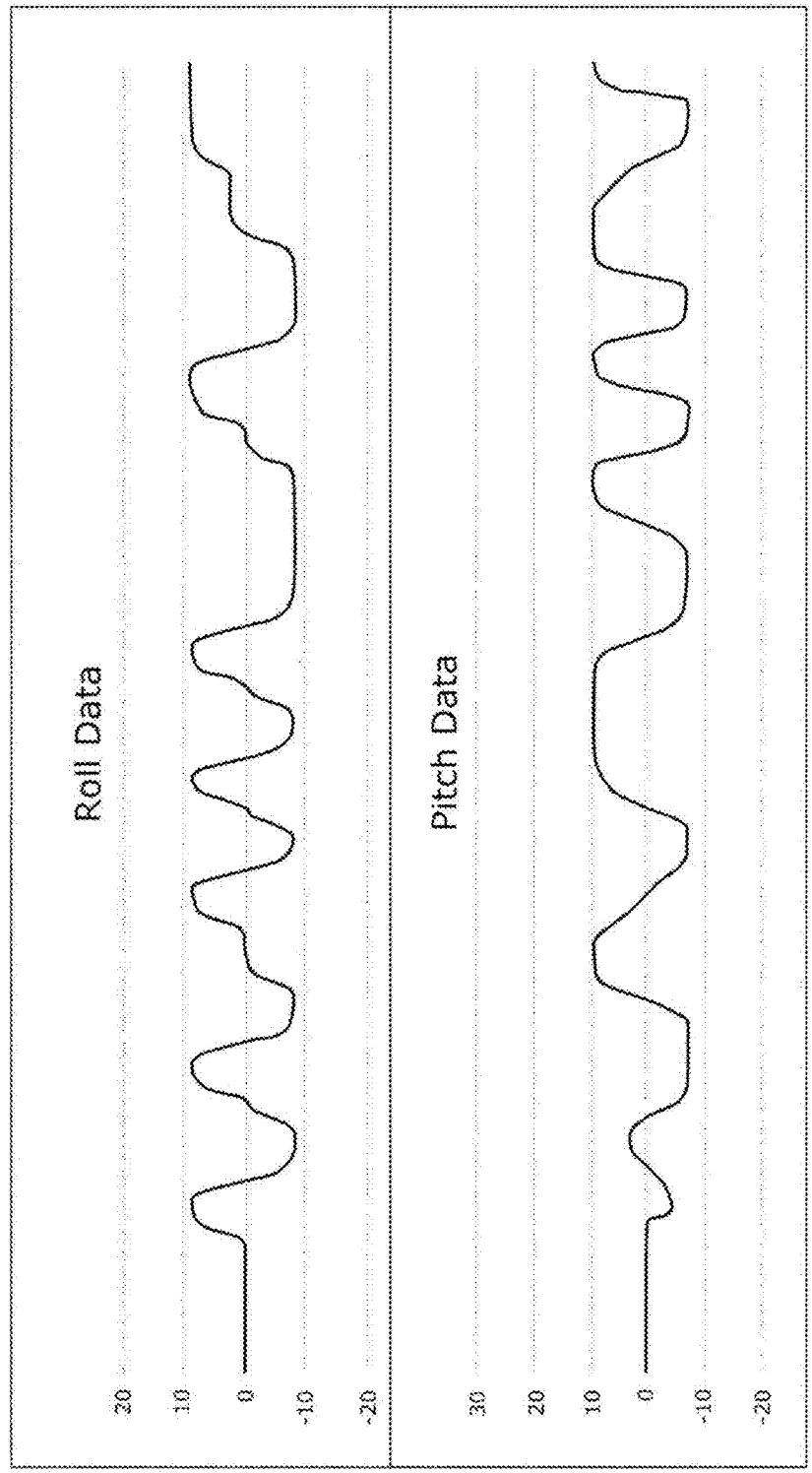
Figure 9:
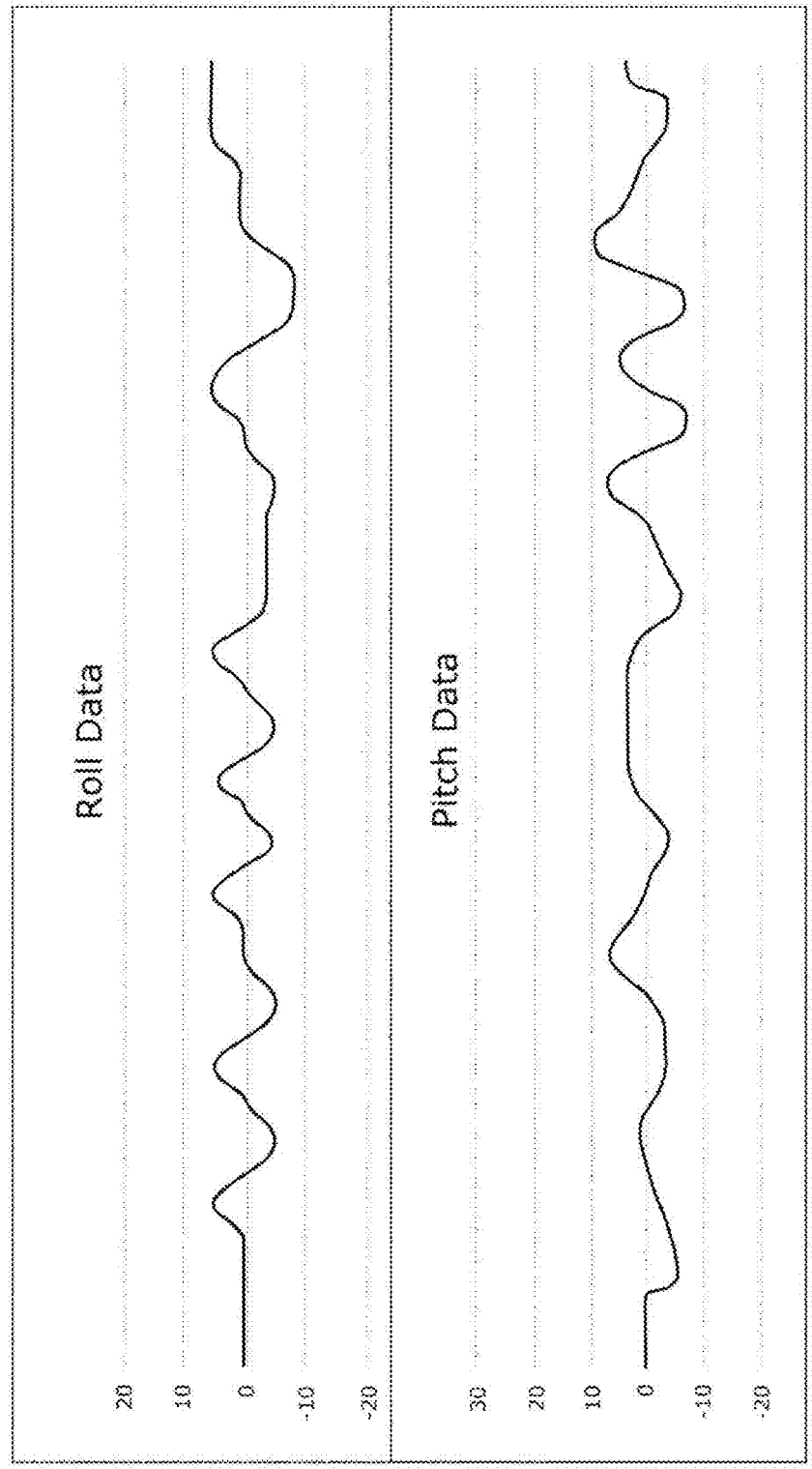

In detail, FIG. 6 shows motion control data, FIG. 7 shows final motion control data obtained by applying a magnification value of 1.0, FIG. 8 shows final motion control data obtained by applying a magnification value of 1.5, and FIG. 9 shows final motion control data obtained by applying a magnification value of 0.5.

As seen from FIG. 5 showing a comprehensive graph, the amplitude of a plot of the final motion control data obtained by applying a magnification value of 0.5 may be reduced but the number of cases in which the motion device 310 completely stops moving (a slope of a plot is 0) may be reduced.

The aforementioned procedure may be the same as in filtering processing.

For example, when the motion device 310 is controlled using corresponding final motion control data when VR content is reproduced after final motion control data is generated and stored by performing low pass filter processing of the frequency domain on motion control data in a specific section including the motion sickness-causing section, the motion device 310 may reduce speed of movement (frequency amplitude) and may reduce the likelihood of exceeding a motion range compared with the case in which motion control data using existing content motion data is used, thereby further reducing the likelihood of motion sickness.

In addition, after the final motion control data obtained by subtracting a positive delay value from motion control data in a specific section including the motion sickness-causing section is generated and stored, even if movement occurs in actual VR convent when VR content is reproduced, the case in which movement of the motion device 310 does not occur may be prevented, thereby preventing the likelihood of motion sickness of a VR content viewer.

In the aforementioned embodiment, although a procedure of automatically performing selection of the motion sickness-causing section and generation of the final motion control data by the motion sickness reduction apparatus 100 has been described, the motion sickness reduction apparatus 100 may provide a type of authoring tool and may process selection of the motion sickness-causing section and generation of the final motion control data according to user input.

For example, the final motion control data generator 150 of FIG. 2 may receive correction of the motion control data through a function of the authoring tool from the user and may generate the final motion control data using the corrected and received motion control data.

In this case, the motion sickness-causing section selector 140 of FIG. 2 may control an equipped display unit to display the motion sickness-causing section based on a difference between the motion control data and the motion detection data.

That is, a manager may check a plot over time of the motion control data, a plot over time of the motion detection data, and the motion sickness-causing section displayed based on a difference therebetween from the display unit, and may directly change the plot on the time axis of the motion control data in the corresponding motion sickness-causing section, and the changed graph may become the final motion control data.

Figure 4:
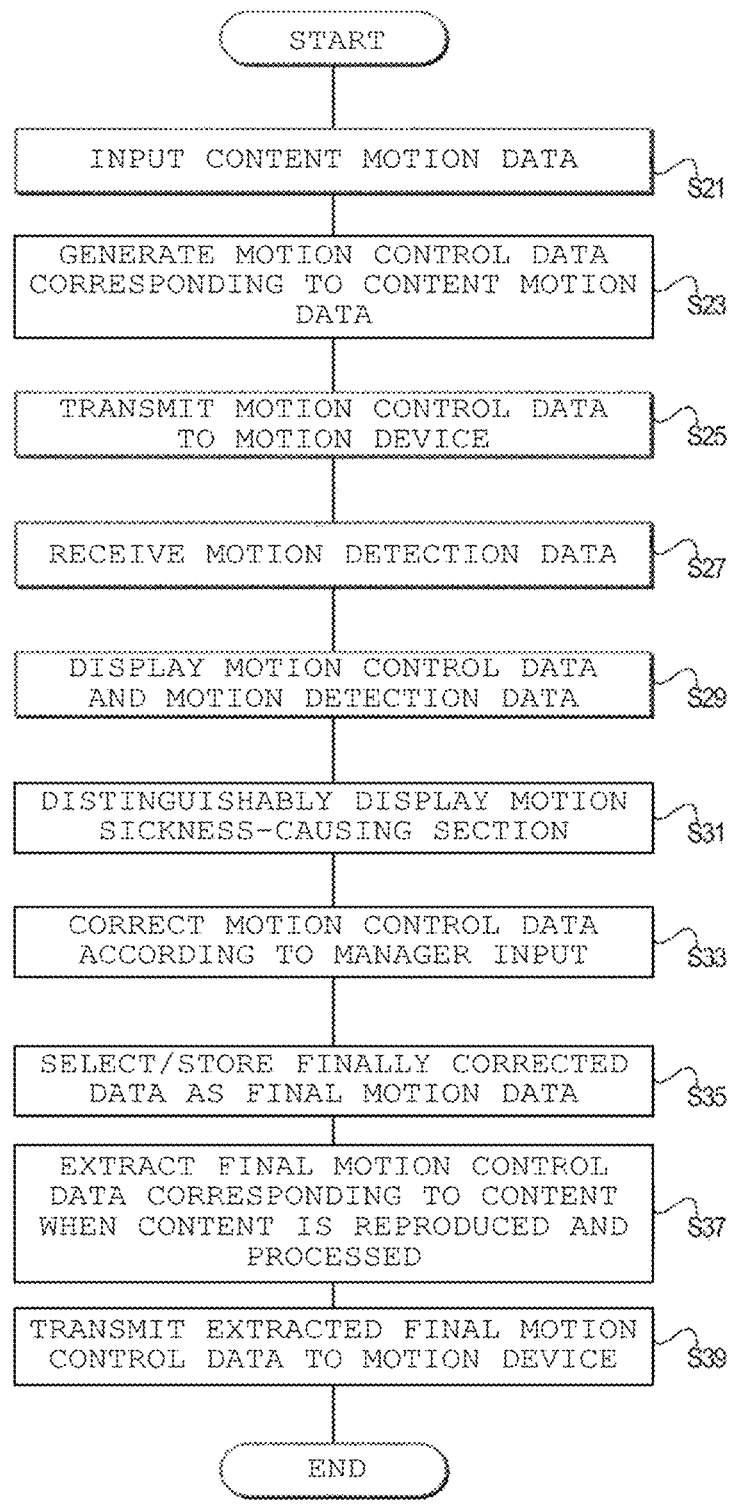

As such, an overall procedure of generating the final motion control data through manual manipulation of the manager is shown in FIG. 4. In a description of the present embodiment, the motion sickness reduction apparatus 100 may be assumed to reproduce a type of authoring tool and to perform the following operations according to manager selection.

The motion sickness reduction apparatus 100 may receive content motion data from the VR content reproduction apparatus 200 and may generate motion control data corresponding to the content motion data. Such a procedure may be performed as the manager reproduces specific VR content.

Then, the motion sickness reduction apparatus 100 may transmit the generated motion control data to the motion device 310, and as described above, when the motion device 310 is not controlled directly, the generated motion control data may also be transmitted to the motion platform 300.

Accordingly, the motion device 310 may be driven, and in this case, the motion sickness reduction apparatus 100 may receive the motion detection data from the sensing device 320 or a sensor for detecting an operation or driving state of the motion device 310.

Then, the motion sickness reduction apparatus 100 may simultaneously display the motion control data and the motion detection data on a screen of a manager.

In this case, the motion sickness reduction apparatus 100 may select the motion sickness-causing section based on a difference between the motion control data and the motion detection data and may then display the motion sickness-causing section to be distinguished from other sections on the screen. For example, the motion sickness-causing section may be displayed to be distinguished from other sections by applying specific color.

Needless to say, the motion sickness-causing section may be selected directly by the manager.

Then, the manager may directly change a plot of the motion control data displayed on the screen using a data input method or a graphical method, and the motion sickness reduction apparatus 100 may correct the motion control data according to manager input for change and may determine and store the finally corrected data as the final motion control data.

Then, when VR content is reproduced and processed, the motion sickness reduction apparatus 100 may extract the final motion control data corresponding to the VR content from the storage 160 and may transmit the same to the motion device 310 or the motion platform 300.

In the aforementioned embodiment, an example in which the motion sickness reduction apparatus 100, the VR content reproduction apparatus 200, and the motion platform 300 are configured as independent devices has been described, at least two there among may be integrated into one device, needless to say.

Needless to say, the aforementioned procedures for performing the embodiments may be performed using a program or an application stored in a predetermined recording medium (e.g., which is readable by a computer). Here, the recording medium may include an electronic recording medium such as a random access memory (RAM), a magnetic recording medium such as a hard disk, and an optical recording medium such as a compact disc (CD).

In this case, the program stored in the recording medium may be executed on hardware such as a computer or a smartphone and may be used to perform the aforementioned embodiments. In particular, at least one of functional blocks of the aforementioned motion sickness reduction apparatus according to the present invention may be embodied by the program or the application.

While this invention has been particularly shown and described with reference to exemplary embodiments thereof, it will be understood by those skilled in the art that various changes in form and details may be made therein without departing from the spirit and scope of the invention as defined by the appended claims. The exemplary embodiments should be considered in a descriptive sense only and not for purposes of limitation. Therefore, the scope of the invention is defined not by the detailed description of the invention but by the appended claims, and all differences within the scope will be construed as being included in the present invention.

INDUSTRY AVAILABILITY

As described above, the present invention may minimize dizziness, that is, motion sickness of a user who uses immersive VR content, which occurs due to a difference between movement on a screen of VR content and actual movement of the body.

The invention claimed is:

1. A control method of a motion sickness reduction apparatus for a virtual reality (VR) motion platform, the method comprising:
(a) receiving content motion data included in VR content;
(b) transmitting motion control data corresponding to the content motion data received in operation (a) to a motion device and controlling motion of the motion device;
(c) receiving motion detection data corresponding to a motion state of the motion device from a predetermined sensing device;
(d) selecting a motion sickness-causing section using a difference between the motion control data and the motion detection data;
(e) generating final motion control data for minimizing a degree of motion sickness in the motion sickness-causing section selected in operation (d) during a preset content reproduction section according to a preset algorithm and storing the final motion control data; and
(f) transmitting the final motion control data stored in operation (e) to the motion device and controlling the motion of the motion device when three-dimensional (3D) VR content is reproduced and processed, wherein:
operation (d) includes selecting a motion sickness-causing section based on a section in which a size of the motion detection data is not changed while a size of the motion control data is changed; and
operation (e) includes adjusting the motion control data to continuously change the size of the motion detection data in the motion sickness-causing section and generating the adjusted motion control data as the final motion control data.

2. The method of claim 1, wherein:
operation (e) includes calculating the final motion control data by multiplying the motion control data in a specific section including the motion sickness-causing section by a magnification value equal to or less than 1.

3. The method of claim 2, wherein the magnification value is dynamically calculated in consideration of the difference between the motion control data in the motion sickness-causing section and the motion detection data and a size of the motion control data in a specific section including the motion sickness-causing section.

4. The method of claim 1, wherein:
operation (e) includes generating the final motion control data by performing filtering processing of a frequency domain on the motion control data in the specific section including the motion sickness-causing section.

5. The method of claim 1, further comprising: providing a user authoring tool, wherein:
operation (d) includes controlling an equipped display unit to display the motion sickness-causing section based on the difference between the motion control data and the motion detection data; and
operation (e) includes (e1) receiving correction of the motion control data through a function of the authoring tool from a user, and (e2) generating the final motion control data using the motion control data corrected and received in operation (d1).

6. The method of claim 1, wherein:
the motion device is a device for performing three-dimensional (3D) movement; and the motion control data and the final motion control data are used to control the motion device to perform at least one of X-axis rotation, Y-axis rotation, or Z-axis rotation in three-dimensional (3D) coordinates.

7. A control method of a motion sickness reduction apparatus for a virtual reality (VR) motion platform, the method comprising:
(a) receiving content motion data included in VR content;
(b) transmitting motion control data corresponding to the content motion data received in operation (a) to a motion device and controlling motion of the motion device;
(c) receiving motion detection data corresponding to a motion state of the motion device from a predetermined sensing device;
(d) selecting a motion sickness-causing section using a difference between the motion control data and the motion detection data;
(e) generating final motion control data for minimizing a degree of motion sickness in the motion sickness-causing section selected in operation (d) during a preset content reproduction section according to a preset algorithm and storing the final motion control data, and
(f) transmitting the final motion control data stored in operation (e) to the motion device and controlling the motion of the motion device when three-dimensional (3D) VR content is reproduced and processed, wherein:
operation (d) includes selecting the motion sickness-causing section based on a section in which a difference between change in the motion control data and change in the motion detection data is equal to or less than a preset value; and
operation (e) includes adjusting the motion control data to increase the change in the motion detection data in the motion sickness-causing section compared with a preset value and generating the adjusted motion control data as the final motion control data.

8. A motion sickness reduction apparatus for a virtual reality (VR) motion platform, the apparatus comprising:
a content motion data input unit configured to receive content motion data included in VR content;
a motion device controller configured to transmit motion control data corresponding to the content motion data received by the content motion data input unit to a motion device and controlling motion of the motion device;
a sensing data receiver configured to receive motion detection data corresponding to a motion state of the motion device from a predetermined sensing device;
a motion sickness-causing section selector configured to select a motion sickness-causing section using a difference between the motion control data and the motion detection data; and
a final motion control data generator configured to generate final motion control data for minimizing a degree of motion sickness in the motion sickness-causing section selected by the motion sickness-causing section selector according to a preset algorithm and to store the final motion control data,
wherein the motion device controller transmits the final motion control data to the motion device and controls motion of the motion device when three-dimensional (3D) VR content is reproduced and processed.

9. The motion sickness reduction apparatus of claim 8, wherein the motion sickness-causing section selector selects a motion sickness-causing section based on a section in which a size of the motion detection data is not changed while a size of the motion control data is changed, adjusts the motion control data to continuously change the size of the motion detection data in the motion sickness-causing section, and generates the adjusted motion control data as the final motion control data.

10. The motion sickness reduction apparatus of claim 8, wherein:
   the motion sickness-causing section selector selects the motion sickness-causing section based on a section in which a difference between change in the motion control data and change in the motion detection data is equal to or less than a preset value; and
   the final motion control data generator adjusts the motion control data to increase the change in the motion detection data in the motion sickness-causing section compared with a preset value and generates the adjusted motion control data as the final motion control data.

11. The motion sickness reduction apparatus of claim 9, wherein the final motion control data generator calculates the final motion control data by multiplying the motion control data in a specific section including the motion sickness-causing section by a magnification value equal to or less than 1.

12. The motion sickness reduction apparatus of claim 11, wherein the magnification value is dynamically calculated in consideration of the difference between the motion control data in the motion sickness-causing section and the motion detection data and a size of the motion control data in a specific section including the motion sickness-causing section.

13. The motion sickness reduction apparatus of claim 9, wherein the final motion control data generator generates the final motion control data by performing filtering processing of a frequency domain on the motion control data in the specific section including the motion sickness-causing section.

14. The motion sickness reduction apparatus of claim 8, wherein:
   the motion sickness-causing section selector controls an equipped display unit to display the motion sickness-causing section based on the difference between the motion control data and the motion detection data; and
   the final motion control data generator receives correction of the motion control data through a function of an authoring tool from a user, and generates the final motion control data using the corrected and received motion control data.

15. The motion sickness reduction apparatus of claim 8, wherein:
   the motion device is a device for performing three-dimensional (3D) movement; and
   the motion control data and the final motion control data are used to control the motion device to perform at least one of X-axis rotation, Y-axis rotation, or Z-axis rotation in three-dimensional coordinates.

* * * * *